United States Patent [19]

Nagubandi

[11] Patent Number: 4,548,760
[45] Date of Patent: Oct. 22, 1985

[54] PROCESS FOR PREPARING PHOSPHONOMETHYLATED AMINO ACIDS

[75] Inventor: Sreeramulu Nagubandi, Bedford Hills, N.Y.

[73] Assignee: Stauffer Chemical Company, Westport, Conn.

[21] Appl. No.: 657,561

[22] Filed: Oct. 4, 1984

Related U.S. Application Data

[62] Division of Ser. No. 489,627, Apr. 28, 1983, Pat. No. 4,491,548.

[51] Int. Cl.$^4$ ............................................. C07F 9/38
[52] U.S. Cl. ..................... 260/502.5 F; 260/465.5 R; 260/938; 560/171; 562/555
[58] Field of Search .................. 260/502.5 F, 465.5 R; 560/171; 562/555

[56] References Cited

U.S. PATENT DOCUMENTS

| | | | |
|---|---|---|---|
| 2,328,358 | 8/1943 | Pikl | 260/502.5 E |
| 3,160,632 | 12/1964 | Toy et al. | 260/502.5 F |
| 3,288,846 | 11/1966 | Irani et al. | 260/502.5 F |
| 3,799,758 | 3/1974 | Franz | 260/502.5 F |
| 3,991,095 | 11/1976 | Gaertner | 260/455 A |
| 4,035,177 | 7/1977 | Gaertner | 71/87 |
| 4,251,258 | 2/1981 | Kaufman | 260/502.5 F |

OTHER PUBLICATIONS

Franz, J. E., "Glyphosphate and Related Chemistry," Monsanto Agricultural Products Co., St. Louis, Mo. 63166, United States, Adv. Pesticide Sci. Plenary Lect. Symp. Pap. Int. Congr. Pesticide Chem., 4th 1978, (Pub. 1979), vol. 2, pp. 139–137.

Primary Examiner—J. E. Evans
Attorney, Agent, or Firm—Hensley M. Flash

[57] ABSTRACT

A process for preparing phosphonomethylated amino acids comprising phosphonomethylating an N-carbamylated amino acid derivative with formaldehyde and a phosphorus source to obtain a phosphonomethylated N-carbamylated amino acid derivative which is then hydrolyzed to the corresponding phosphonomethylated amino acid, e.g. glyphosate, or acid derivative.

8 Claims, No Drawings

PROCESS FOR PREPARING PHOSPHONOMETHYLATED AMINO ACIDS

This is a division of application Ser. No. 489,627, filed Apr. 28, 1983, now U.S. Pat. No. 4,491,548.

FIELD OF THE INVENTION

The present invention is a process for preparing phosphonomethylated amino acids, and, in particular, for preparing N-phosphonomethylglycine, otherwise known as glyphosate.

BACKGROUND OF THE INVENTION

Certain phosphonomethylated amino acids, e.g. glyphosate and its derivatives, are herbicides. Herbicides are useful for controlling or modifying plant growth. Glyphosate and its derivatives are effective in controlling or modifying growth in a wide variety of plant species, including broadleaves, grasses and sedge.

Because glyphosate and its derivatives are so important, new processes for making it and its derivatives faster, cheaper or in greater yields are constantly in demand. A new process for preparing glyphosate and its derivatives has now been discovered.

BRIEF DESCRIPTION OF THE INVENTION

It has now been discovered that certain N-carbamylated amino acid derivatives can be used to prepare phosphonomethylated amino acids such as glyphosate. As used herein, an "N-carbamylated amino acid derivative" includes an N-carbamylated amino acid and its derivatives, an N-thiocarbamylated amino acid and its derivatives, an N-thionocarbamylated amino acid and its derivatives and an N-dithiocarbamylated amino acid and its derivatives.

Phosphonomethylated amino acids can be prepared from these N-carbamylated amino acid derivatives by phosphonomethylating at the nitrogen to obtain a phosphonomethylated N-carbamylated amino acid derivative; and hydrolyzing said phosphonomethylated N-carbamylated amino acid derivative to obtain a phosphonomethylated amino acid or its derivative.

The N-carbamylated amino acid derivatives of the present invention have the structure:

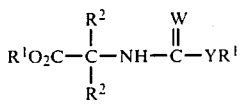

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen; $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive, alkoxyalkoxy having 2 to 8 carbon atoms, inclusive; and a heterocyclic group having 2 to 12 carbon atoms, inclusive; and W and Y are independently selected from the group consisting of oxygen and sulfur.

The process is illustrated by the preparation of glyphosate or its derivatives, however other phosphonomethylated amino acids or their derivatives can be prepared by the process. In one preferred embodiment, the process comprises: suspending glycine or glycine ethyl ester hydrochloride in a solvent to obtain a suspension; bubbling phosgene gas through said suspension to form an isocyanate; reacting said isocyanate with methanol or ethanol to obtain an N-carbamylated glycine derivative; phosphonomethylating said N-carbamylated glycine derivative to obtain a phosphonomethylated N-carbamylated glycine derivative; and hydrolyzing said phosphonomethylated N-carbamylated glycine derivative to obtain glyphosate.

In another preferred embodiment, the process comprises: dissolving phosgene gas in a solvent to obtain a phosgene-containing solvent; adding glycine or glycine ethyl ester hydrochloride dissolved in triethylamine to said phosgene-containing solvent to form a carbamyl chloride; reacting said carbamyl chloride with methanol or ethanol to obtain an N-carbamylated glycine derivative; phosphonomethylating said N-carbamylated glycine derivative to obtain a phosphonomethylated N-carbamylated glycine derivative; and hydrolyzing said phosphonomethylated N-carbamylated glycine derivative to obtain glyphosate.

DETAILED DESCRIPTION OF THE INVENTION

In a step leading to this process, an N-carbamylated amino acid derivative is prepared. A method of preparation includes: suspending a primary amino acid derivative in a solvent to obtain a suspension; bubbling phosgene gas through said suspension to form an isocyanate; and reacting said isocyanate with an alcohol to obtain the N-carbamylated amino acid derivative.

Another method of preparing an N-carbamylated amino acid derivative includes: dissolving phosgene gas in a solvent to obtain a phosgene-containing solvent; adding a primary amino acid derivative dissolved in triethylamine to said phosgene-containing solvent to form a carbamyl chloride; and reacting said carbamyl chloride with an alcohol to obtain the N-carbamylated amino acid derivative.

The primary amino derivatives used in the above methods of preparing an N-carbamylated amino acid derivative has the structure:

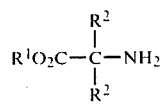

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen; and $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive, phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

An N-carbamylated amino acid derivative has the structure:

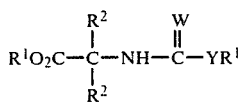

wherein $R^1$ and $R^2$ are defined above; and W and Y are independently selected from the group consisting of oxygen and sulfur. When W and Y are both oxygen, the acid derivative is N-carbamylated; when W is oxygen and Y is sulfur, the acid derivative is N-thiocarbamylated; when W is sulfur and Y is oxygen, the acid derivative is N-thionocarbamylated; and, when W and Y are both sulfur, the acid derivative is N-dithiocarbamylated. For purposes of this application, all four of these acids are referred to as "N-carbamylated amino acid derivatives".

The following reactions illustrate the present invention:

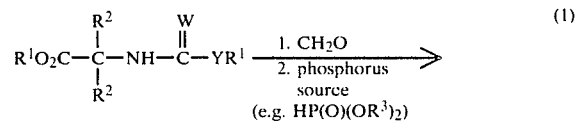 (1)

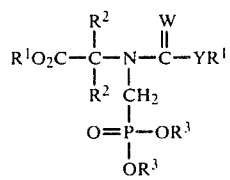

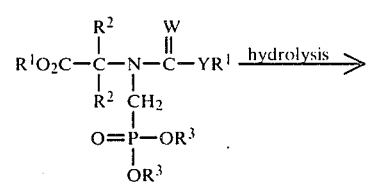 (2)

-continued

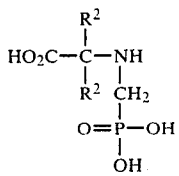

(glyphosate when $R^2$ = H)

In reaction (1) an N-carbamylated amino acid derivative is phosphonomethylated at the nitrogen using formaldehyde and a phosphorus source.

In reaction (2) the phosphonomethylated N-carbamylated amino acid derivative is hydrolyzed to obtain a phosphonomethylated amino acid (e.g. glyphosate when $R^2$=H) or acid derivative.

In reactions (1) and (2), $R^1$, $R^2$, W and Y are as defined above. The phosphorus source is selected from the group consisting of:

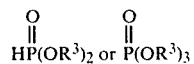

wherein $R^3$ is selected independently each time it occurs from the group consisting of hydrogen, alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

Suitable N-carbamylated amino acid derivatives for use in this process can be formed from, e.g. carbamyl halides, isocyanates, thiocarbamyl halides, isothiocyanates, chlorothioformates, chlorodithioformates, and sodium dithiocarbamate or other dithiocarbamate salts. Carbamyl chlorides and isocyanates can be formed, for example, by reacting an appropriate (as defined above) primary amino acid derivative with phosgene. Thiocarbamyl chlorides and isothiocyanates can be formed, for example, by reacting an appropriate (as defined above) primary amino acid derivative and thiophosgene. Alternatively, isothiocyanates can be formed from dithiocarbamate salts, which can be prepared by reacting an appropriate (as defined above) amino acid derivative with carbon disulfide in the presence of a base such as sodium hydroxide or triethylamine.

In the method of preparing an N-carbamylated amino acid derivative wherein an appropriate (as defined above) primary amino acid derivative is suspended in a solvent, a suitable solvent can include, e.g. water, or ethanol or other organic solvents such as toluene or tetrahydrofuran or acetonitrile.

Phosgene (a gas) can then be bubbled through the primary amino acid derivative suspended in the solvent. The reaction mixture should be heated to reflux and stirred while the phosgene is added. The resultant product will be isocyanates or carbamyl chlorides depending on the extent of heating. Thiophosgene can be used as an alternative to phosgene.

Nitrogen gas can then be bubbled through the reaction mixture containing the isocyanates to remove excess phosgene gas. Alternatively, excess phosgene can be removed by creating a vacuum over the reaction mixture. The reaction mixture can be filtered, optionally, to yield an isocyanate filtrate.

Other amino acid derivative isocyanates can also be prepared by other routes. For example, glycine isocyanates or their salts can be prepared by reacting chloroacetic acid (or its derivatives) with sodium cyanate (in 1 to 2 molar excess) in an anhydrous solvent. Examples of solvents include, but are not limited to, acetonitrile and toluene. Sodium thiocyanate would give the glycine isothiocyanate (corresponding to W=S).

One to two mole equivalents of a simple alcohol, such as methanol or ethanol, can then be added to the resulting isocyanate filtrate at room temperature with stirring. The resulting reacting is exothermic and an N-carbamylated amino acid derivative is formed that is suitable for carrying out the processes of the present invention.

In the alternate method of preparing an N-carbamylated amino acid derivative wherein phosgene gas is dissolved in a solvent, a suitable solvent can include toluene or tetrahydrofuran or acetonitrile. At least one mole equivalent of phosgene gas is dissolved in the solvent by bubbling said gas through the solvent at room temperature or below with stirring. The amount of dissolved phosgene can be determined by weighing the solvent before and after the addition of phosgene. A suitable primary amino acid derivative (as defined above), dissolved in about two or more mole equivalents of triethylamine, is then added to the phosgene solution at room temperature or below with stirring. The resultant product is a mixture of carbamyl chloride and triethylamine hydrochloride.

The carbamyl chloride can be dissolved in an inert solvent, e.g. toluene, so that the triethylamine hydrochloride can be separated from the mixture by filtration. One to two mole equivalents of a simple alcohol, such as methanol or ethanol, can then be added to the resulting carbamyl chloride filtrate at room temperature with stirring. After removal of the solvent, the resulting product is an N-carbamylated amino acid derivative that is suitable for carrying out the processes of the present invention.

If the carbamyl chloride is dissolved in a solvent such as tetrahydrofuran or acetonitrile, the alcohol can be added first to prepare the N-carbamylated amino acid derivative. Then the triethylamine salt may be removed. This N-carbamylated amino acid derivative is suitable for carrying out the processes of the present invention.

A primary amino acid derivative containing an N-dithiocarbamate group can be prepared by reacting a primary amino acid derivative in a solvent, with at least one mole equivalent or more of carbon disulfide in the presence of a suitable base. Suitable bases include, e.g., sodium hydroxide, potassium hydroxide and triethylamine. Suitable solvents include, e.g., simple alcohols, e.g., methanol or ethanol and water. The resulting product is the corresponding salt of an N-dithiocarbamylated amino acid. This N-dithiocarbamate salt can be alkylated on the sulfur with a variety of suitable alkylating agents. Suitable alkylating agents include, e.g., methyl halide and trimethyl phosphite, in which case the N-dithiocarbamate is methylated. This N-dithiocarbamylated amino acid derivative is suitable for carrying out the processes of this invention.

The N-carbamylated amino acid derivatives prepared by the above procedures can be phosphonomethylated in accordance with the processes of the present invention. The phosphonomethylation can be carried out by adding formaldehyde and a phosphorus source in the presence of a suitable acid or acid anhydride.

Suitable acids or anhydrides include but are not limited to, hydrochloric acid, acetic acid, and acetic anhydride. The formaldehyde may be used in the form of aqueous formaldehyde or solid paraformaldehyde. The mole ratio of N-carbamylated amino acid derivative to formaldehyde can generally range up to about a 1:10 with about a 1:3 mole ratio being desirable and about a 1:1.5 mole ratio being preferable. Mole ratios above 1:10 are usually not economical.

The formaldehyde may be added slowly to the N-carbamylated amino acid derivative at temperatures generally ranging from about 5° C. to about 80° C. with a range of from about 5° C. to about 40° C. being desirable and a range of from about 5° C. to about 20° C. being preferable.

After the formaldehyde is added, the reaction mixture is stirred, preferably at least for an hour, at room temperature or at a temperature up to about 60°–80° C.

The phosphorus source is selected as defined above. The mole ratio of N-carbamylated amino acid derivative to phosphorus source can generally range up to about a 1:10 mole ratio, with about a 1:3 mole ratio being desirable and about a 1:1.5 mole ratio being preferable. Mole ratios above 1:10 are usually not economical. The phosphorus source can be added directly to the flask containing the N-carbamylated amino acid derivative and formaldehyde reaction mixture. This reaction mixture is heated to reflux, preferably for two to three hours.

The solvent can then be removed from the phosphonomethylated N-carbamylated amino acid derivative by heating under vacuum or other means which are known for separating solvents from reaction mixtures. The phosphonomethylated N-carbamylated amino acid derivative is then hydrolyzed in the presence of an acid or a base.

When an acid is used in the hydrolysis step, the phosphonomethylated N-carbamylated amino acid derivative is heated preferably to reflux temperature in the presence of a suitable strong acid. Generally, a range of about 4 moles to about 15 moles of acid can be used, with from about 4 moles to about 10 moles being desirable and about 4 moles to about 6 moles being preferable. Typically, at reflux temperatures, the reaction time ranges from about one hour to about ten hours, with about one hour to about five hours being desirable and about one hour to about three hours being preferable. Suitable strong acids include, but are not limited to, hydrochloric acid, sulfuric acid and nitric acid.

When a base is used in the hydrolysis step, the phosphonomethylated N-carbamylated amino acid derivative is heated preferably to reflux temperature in the presence of a suitable strong base. Generally, a range of about 4 moles to about 15 moles of base can be used, with from about 4 moles to about 10 moles being desirable and about 4 moles to about 6 moles being preferable. Typically, at reflux temperatures, the reaction time ranges from about one hour to about ten hours, with about one hour to about five hours being desirable and about one hour to about three hours being preferable. Suitable strong bases include, but are not limited to, sodium hydroxide and potassium hydroxide. Finally, the pH of the basic reaction mixture can then be adjusted to about pH 4 using hydrochloric acid or other acid. Evaporation of the solvent yields a phosphonomethylated amino acid or acid derivative.

The following examples show practical applications of the processes described. The final products obtained in each Example is glyphosate ($R^1$ and $R^2$ are hydrogens).

EXAMPLE 1

Synthesis of Glyphosate Via N-carboethoxymethyl-S-methyl dithiocarbamate

A solution of glycine ethyl ester (50 g, 0.358 mole) in anhydrous methanol (225 ml) and a solution of sodium hydroxide (28.7 g, 0.716 mole) in methanol (65 ml) were simultaneously added to carbon disulfide (32.7 g, 0.429 mole) at room temperature. The reaction was exothermic.

The reaction mixture was stirred for 2 hrs. and the solid formed was filtered. The filtrate was evaporated and redissolved in anhydrous methanol (100 ml) then to this reaction mixture trimethyl phosphite (48 ml) was added. The reaction mixture was kept under nitrogen atmosphere. The glycine ethyl ester dithiocarbamate obtained was phosphonomethylated without further purification.

To the above reaction mixture, paraformaldehyde (12.9 g, 0.429 mole), acetic anhydride (40.6 ml) and acetic acid (35 ml) were added. The reaction was stirred at reflux for 2 hrs. and the solvent was removed. This oily material was refluxed in a solution of sodium hydroxide, followed by concentrated hydrochloric acid, to obtain glyphosate along with sodium chloride. The sodium chloride was removed to obtain glyphosate.

EXAMPLE 2

1. Synthesis of N-carbomethoxyglycine ethyl ester isocyanate

A solution of phosgene (78.2 g., 1.79 mole) in dry toluene (200 ml) was placed in a three neck flask equipped with a thermometer, reflux condenser and arteries of traps, containing sodium hydroxide, and water. Glycine ethyl ester hydrochloride (55.1 g, 0.395 mole) was added at once. The reaction mixture was refluxed for 3 hrs., during which time HCl gas evolved. The unreacted glycine ethyl ester hydrochloride was filtered and the filtrate containing glycine ethyl ester isocyanate (IR 2250 $cm^{-1}$) was reacted with an excess of anhydrous methanol for 0.5 hrs. then the solvent was evaporated to obtain N-carbomethoxyglycine ethyl ester.

*Alternatively*, glycine ethyl ester hydrochloride (40.1 g, 0.28 mole) suspended in dry tetrahydrofuran (200 ml) and phosgene were bubbled through the reaction mixture for 0.5 hrs, as the reaction mixture was refluxed. At the end of 0.5 hrs., the reaction was cooled to room temperature and toluene was added followed by the distillation of THF. The reaction mixture containing toluene was further refluxed for 1 hr. The unreacted glycine ethyl ester hydrochloride was filtered and the filtrate containing glycine ethyl ester isocyanate (IR 2250 $cm^{-1}$) was reacted with excess (2-3 mole) anhydrous methanol and, when the isocyanate peak disappeared, the solvent was removed to isolate N-carbomethoxyglycine ethyl ester.

*Alternatively*, glycine ethyl ester hydrochloride (35.7 g, 0.256 mole) was suspended in dry acetonitrile (300 ml) containing phosgene (50.7 g, 0.512 mole) and the reaction mixture was refluxed. A few drops of dry pyridine was added after 1 hr. of refluxing. Unreacted glycine ethyl ester hydrochloride was filtered off and dry toluene (300 ml) was added then acetonitrile was distilled off. The toluene solution was refluxed for 1 hr. to obtain glycine ethyl ester isocyanate (IR 2250 $cm^{-1}$). This isocyanate was reacted, without further purification, with anhydrous methanol.

2. Synthesis of N-carbomethoxy glycine ethyl ester (via carbamyl chloride)

To a solution of phosgene (70.4 g, 0.71 mole) in dry toluene (300 ml), a mixture of glycine ethyl ester hydrochloride (99.1 g, 0.71 mole) and triethylamine (158 g, 1.56 mole) was slowly added at 0° C. The reaction was exothermic. After 2 hrs. of stirring, anhydrous methanol was added to the reaction mixture and stirring was continued for another 0.5 hrs. The reaction mixture was partitioned between water and chloroform, then the pH of the solution was adjusted to 4 with concentrated HCl. The chloroform layer was dried and the solvent was evaporated to obtain the N-carbomethoxy glycine ethyl ester with the structure being confirmed by spectroscopy.

*Alternatively*, phosgene (50.1 g, 0.5 mole) was dissolved in dry acetonitrile (300 ml) in a three-neck, one liter, flask equipped with thermometer and magnetic stirrer. Glycine ethyl ester hydrochloride (70.6 g, 0.5 mole), partially dissolved in triethylamine (111.1 g, 1.1 mole) was carefully added to the above phosgene solution at 0° C. The light brown reaction mixture was cooled over ice and stirred for 2 hrs. Anhydrous methanol was added to the reaction mixture and the reaction mixture was stirred for 1 hr. The pH of the reaction mixture was adjusted to 4 using hydrochloric acid before it was partitioned between water and chloroform. The organic layer was separated then the solvent was removed to obtain the product which was confirmed by nmr.

3. Synthesis of N-(carbomethoxy)-N-(diphenylphosphonomethyl) glycine ethyl ester A mixture of N-carbomethoxy glycine ethyl ester (10.0 g, 0.06 mole), paraformaldehyde (2.0 g, 0.06 mole), acetic anhydride (96%, 4.0 g, 0.06 mole) and acetic acid (20 ml) was stirred for 3 hrs. at 60°-70° C. under nitrogen. Triphenyl phosphite (19.2 g, 0.03 mole) was slowly added then the reaction mixture was refluxed for 2 hrs. at 110°-200° C. The reaction was cooled and the solvent was evaporated under vacuum. The resulting oily material was dissolved in chloroform and washed with water. The product was confirmed by nmr. Yield 70.5%.

4. Hydrolysis of N-(carbomethoxy)-N-(diphenylphosphonomethyl) glycine ethyl ester The above named compound (2 g, 0.005 mole) was reacted at 50° C. with sodium hydroxide (1.0 g) in water (20 ml) for 2 hrs. The reaction mixture was acidified with hydrochloric acid and ethanol was added. The reaction mixture was concentrated and the precipitated sodium chloride was filtered. The solvent from the filtrate was evaporated to obtain glyphosate.

The above hydrolysis can also be carried out under acid conditions using concentrated hydrochloric acid instead of sodium hydroxide. The procedure is similar to that described above. The product in both cases was confirmed by both nmr ($^{31}P$ and H) and HPLC.

What is claimed is:

1. A process for preparing a phosphonomethylated amino acid comprising:
   phosphonomethylating an N-carbamylated amino acid derivative to obtain a phosphonomethylated N-carbamylated amino acid derivative; and hydrolyzing said phosphonomethylated N-carbamylated amino acid derivative to obtain a phosphonomethylated amino acid or acid derivative wherein said N-carbamylated amino acid derivative is prepared by a process comprising:

suspending a primary amino acid derivative in a solvent to obtain a suspension; bubbling phosgene gas through said suspension to form an isocyanate; and reacting said isocyanate with an alcohol to obtain an N-carbamylated amino acid derivative.

2. A process for preparing a phosphonomethylated amino acid comprising:

phosphonomethylating an N-carbamylated amino acid derivative to obtain a phosphonomethylated N-carbamylated amino acid derivative; and hydrolyzing said phosphonomethylated N-carbamylated amino acid derivative to obtain a phosphonomethylated amino acid or acid derivative wherein said N-carbamylated amino acid derivative is prepared by a process comprising:

dissolving phosgene gas in a solvent to obtain a phosgene-containing solvent; adding a primary amino acid derivative dissolved in triethylamine to said phosgene-containing solvent to form a carbamyl chloride; and reacting said carbamyl chloride with an alcohol to obtain an N-carbamylated amino acid derivative.

3. A process as defined in claim 24 wherein said primary amino acid derivative has the structure:

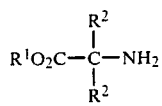

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen; and $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

4. A process as defined in claim 1 wherein said solvent is selected from the group consisting of tetrahydrofuran, acetonitrile and toluene.

5. A process as defined in claim 2 wherein said primary amino acid derivative has the structure:

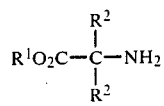

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen; and $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

6. A process as defined in claim 2 wherein said solvent is selected from the group consisting of tetrahydrofuran, acetonitrile and toluene.

7. A process for preparing glyphosate comprising:
suspending glycine or glycine ethyl ester hydrochloride in a solvent to obtain a suspension;
bubbling phosgene gas through said suspension to form an isocyanate;
reacting said isocyanate with methanol or ethanol to obtain an N-carbamylated glycine derivative;
phosphonomethylating said N-carbamylated glycine derivative to obtain a phosphonomethylated N-carbamylated glycine derivative; and
hydrolyzing said phosphonomethylated N-carbamylated glycine derivative to obtain glyphosate.

8. A process for preparing glyphosate comprising:
dissolving phosgene gas in a solvent to obtain a phosgene-containing solvent;
adding glycine or glycine ethyl ester hydrochloride dissolved in triethylamine to said phosgene-containing solvent to form a carbamyl chloride;
reacting said carbamyl chloride with methanol or ethanol to obtain an N-carbamylated glycine derivative;
phosphonomethylating said N-carbamylated glycine derivative to obtain phosphonomethylated N-carbamylated glycine derivative; and
hydrolyzing said phosphonomethylated N-carbamylated glycine derivative to obtain glyphosate.

* * * * *

UNITED STATES PATENT AND TRADEMARK OFFICE
CERTIFICATE OF CORRECTION

PATENT NO. : 4,548,760
DATED : October 22, 1985
INVENTOR(S) : Sreeramulu Nagubandi It is certified that error appears in the above—identified patent and that said Letters Patent is hereby corrected as shown below:

First Page, OTHER PUBLICATIONS, last line, "pp. 139-137" should be "139-147;

Col. 9, Claim 3, first line, "claim 24" should be "claim 1".

Signed and Sealed this

Fourth Day of February 1986

[SEAL]

Attest:

Attesting Officer

DONALD J. QUIGG

Commissioner of Patents and Trademarks